United States Patent [19]

Mittheiss et al.

[11] Patent Number: 5,102,910
[45] Date of Patent: Apr. 7, 1992

[54] PHARMACEUTICAL PREPARATION AND METHOD OF TREATMENT FOR LIVER DYSFUNCTION

[75] Inventors: Elisabeth Mittheiss, Vienna; Werner Gusenbauer, Kottes, both of Austria

[73] Assignee: Homosan AG, Bach, Switzerland

[21] Appl. No.: 521,702

[22] Filed: May 10, 1990

[30] Foreign Application Priority Data

May 11, 1989 [AT] Austria .................................. 1130/89

[51] Int. Cl.$^5$ ..................... A61K 31/16; A61K 31/19; A61K 31/185; A61K 31/315
[52] U.S. Cl. .................................. 514/494; 514/553; 514/557; 514/562; 514/613; 514/811; 514/838; 514/895; 514/894; 424/641
[58] Field of Search ................ 514/494, 613, 562, 894

[56] References Cited

U.S. PATENT DOCUMENTS

| | | | |
|---|---|---|---|
| 4,124,718 | 11/1978 | Giroux et al. | 424/274 |
| 4,255,446 | 3/1981 | Iwao et al. | 424/301 |
| 4,440,788 | 4/1984 | Terayama et al. | 424/320 |
| 4,446,154 | 5/1984 | Osterholm | 424/350 |
| 4,499,076 | 2/1985 | Ohashi et al. | 424/143 |
| 4,758,431 | 7/1988 | Osterholm | 424/149 |
| 4,870,071 | 9/1989 | Ogata et al. | 514/191 |

FOREIGN PATENT DOCUMENTS

58-32850  2/1983  Japan.
59-16817  1/1984  Japan.

Primary Examiner—S. J. Friedman
Assistant Examiner—Terry Wilson
Attorney, Agent, or Firm—Herbert Dubno

[57] ABSTRACT

A pharmaceutical composition for the treatment of a liver disorder, comprising as an effective agent against liver dysfunction, a mixture in effective amounts of the components:
(a) L-Asparaginic acid;
(b) L-Cysteine;
(c) L-Glutaminic acid;
(d) sodium selenate; and
(e) zinc acetate or zinc sulfate in the following proportions: 0.020 to 2.00:0.025 to 1.00:0.025 to 5.00:28.10$^{-6}$ to 500.10$^{-6}$:0.010 to 0.300 by weight.

10 Claims, No Drawings

PHARMACEUTICAL PREPARATION AND METHOD OF TREATMENT FOR LIVER DYSFUNCTION

FIELD OF THE INVENTION

Our present invention relates to a pharmaceutical preparation (composition) for the treatment of liver disorders, also referred to herein as liver dysfunctions, and to a method of treatment of an affected subject for liver dysfunction using the new pharmaceutical composition, and to a prophylactic method of protecting the liver.

BACKGROUND OF THE INVENTION

The composition of the invention can be used for the treatment of metabolic and toxic liver disorders in human and veterinary medicine. It is especially effective for the treatment of alcoholic and toxic liver disorders, hyperammonemia, abstinence syndromes and alcohol delirium, as well as acute and chronic cerebral hypoxia.

Long-alcoholism and/or stress can give rise to a multiplicity of liver disorders. The psychological changes range from simple fatty liver syndromes through a variety of stages of alcohol hepatitis through fibrosis to cirrhosis of the liver.

During alcoholic degradation, the NAD (nicotinamide-adenosine-dinucleotide) proton acceptor is reduced to NADH. Because of the increase in the amount of NADH as a result, the NADH/NAD ratio is increased which limits the citric acid cycle (Krebs cycle).

The deficiency of NAD, limits gluconeogenesis from amino acids.

The alcohol is degraded by the following enzymes: alcohol dehydrogenase, MFOS (mixed-function oxidation system), catalase, NADP (nicotinamide-adenosine-dinucleotide phosphate)-oxidase, xanthinoxidase.

During the breakdown of the alcohol by means of xanthinoxidase and catalase, hydrogen peroxide is produced which liberates free oxygen radical. Acetaldehyde is the end product of all of these metabolic processes. In the degradation of acetaldehyde, the oxygen radical is the main metabolite and causes lipid oxidation.

It has long been believed, in connection with the treatment of alcohol-related states and associated liver disorders, that one must first take into consideration two toxic products, namely, free oxygen radical and acetaldehyde. To combat their toxic effects, the reduced forms of glutathione and other amino acids containing thiol groups, play a very great role. Hepatoxicity and the decrease in glutathione concentrations are directly proportional.

OBJECTS OF THE INVENTION

It is the principal object of this invention to provide an improved pharmaceutical preparation or composition which is especially effective for the treatment of liver disorders resulting from alcohol abuse or stress to cure the disorder or at least to ameliorate it.

Another object of the invention is to provide a composition which is prophylactic against the deterioration of the liver in the presence of toxic agents, for example, alcohol or stress conditions.

Yet another object of the invention is to provide an improved method of treatment of liver disorders whereby the damage to the liver can be prevented or minimized.

DESCRIPTION OF THE INVENTION

These objects and others which will become more readily apparent hereinafter are attained, in accordance with the invention, utilizing a preparation of pharmaceutical composition, comprising as an effective agent against liver dysfunction, a mixture in effective amounts of:

(a) L-Asparaginic acid;
(b) L-Cysteine;
(c) L-Glutaminic acid;
(d) sodium selenate; and
(e) zinc acetate or zinc sulfate, for the treatment of liver disorder.

The L-Asparaginic acid of component (a) is also known as L-α-aminosuccinic acid. The L-Cysteine of component (b) is also known as L-β- mercaptoalanine. The L-Glutaminic acid of component (c) is otherwise known as 1-α-aminoglutaric acid. The sodium selenate has the formula $Na_2SeO_4$.

The zinc acetate and zinc sulfate of component (e) have the formulas $Zn(CH_3CO_2)$ and $ZnSO_4$, respectively.

Advantageously, the pharmaceutical composition, which may be present in any pharmaceutical excipient or carrier suitable for the administration technique, can contain the effective components (a) through (e) in the following proportions: 0.020 to 2.00 : 0.025 to 1.00 : 0.025 to 5.00 : 28 $\cdot 10^{-6}$ to 500 $\cdot 10^{-6}$: 0.010 to 0.30, by weight.

The new liver protective preparation of the invention is therapeutically effective to avoid the metabolic and toxic effects of alcohol abuse and stress syndromes in the liver. The composition reliably increases the ATP level which ensures sufficient energy for the material exchange processes breaking down the alcohol and also appears to tie up the toxic free radicals.

While we do not wish to be bound to any theory as to why these components coact so effectively and are important to the effectivity of one another in the composition, we have found that omission of any one of them can lead to a sharp reduction in the efffectiveness of the product.

The L-Glutaminic acid and the L-Cysteine appear to play an important role in the formation of glutathione which has a particularly significant effect in the detoxification processes in the liver and the concentration of which in the liver cells is reduced by an assortment of xenobiotica, oxidative deteriorating substances and alcohol, thereby tending to reduce the protective effect on the liver cells. Selenium, which is a structural component of glutathione peroxidaze tends to promote protection of the cells against oxidative events. This enzyme, for example, catalyzes the reduction of hydrogen peroxide. It appears that under oxidative stress states, the selenium-containing glutathione peroxidase is the key substance in the antioxidative system. The selenium appears to increase the glutathione concentration. Selenium reduces liver deterioration which might otherwise result from hepatoxic materials.

Histological investigations have shown that the collagen accumulation can be reduced in a prophylactic manner by zinc. Zinc appears to be an effective antifibrotic element.

Asparaginic acid, glutaminic acid and cysteine participate in the synthesis of ATP (adenosine-5'-triphosphate).

By enzymatic processes in the cytoplasm and in the mitocondria of the liver cells, oxalacetic acid is formed from the L-Asparaginic acid and α-ketoglutaric acid is formed form the L-Glutaminic acid.

The α-ketoglutaric acid can via oxalacetic acid be transformed to pyruvic acid or through another reaction path, into succinyl-coenzyme-A to participate in this manner in gluconeogenesis and in energy production.

Keto acids are direct reaction products of citric acid cycle in which oxalacetic acid is the key compound in the gluconeogenesis. The transport of the inorganic phosphorus required for ATP synthesis is effected with the aid of a carrier activated by the thiol group of the L-Cysteine.

The simultaneous use of the three amino acids, according to the invention, by limiting the catalization of protein and fatty acid resulting from the blocking of gluconeogenesis, prevents enrichment in and concentration increases of ketone acids, glycerine and triglycerides.

Simultaneously the combination of active ingredients of the invention appears to improve the activity of the ion transport mechanism, the intensity of biosynthetic processes and osmotic functions.

The concentration increase of L-Glutaminic acid metabolites and L-Asparaginic acid metabolites reduces the intensity of glycologisis in the cytoplasmic region. Because of the functional interrelationship of the citric acid cycle and the urea cycle, there is an improvement in the mechanism of ammonia elimination in parallel with the mitochondrial oxidative phosphorylation.

The new liver protective composition of the invention has advantage that is can consist only of natural ingredients and practically has no toxicity so that it can be used in high dosages even in patients suffering from kidney insufficiency.

A suitable dosage form can be used, for example, to administer the composition in terms of 0.1 g of a L-Asparaginic acid per 50 kg of patient's weight per day to substantially 15 g of L-Asparaginic acid per 50 kg of body weight per day (the other components being in proportions as indicated). The treatment may be continued as long as the liver dysfunction manifestations exist, i.e. over periods of weeks or months, and at the lower dosage end of the scale, can be use prophylactically even in cases where there is no liver dysfunction but the patient's habits are such as to warrant prophylactic treatment. The dosage forms will depend upon the mode of administration and both enteral, e.g. oral, and parenteral, e.g. intravenous infusion, may be used.

It also may be mentioned in summary that the three amino acids, L-Asparaginic acid, L-Glutaminic acid and L-Cysteine provide an advantageous increase in the ATP level which is desirable for biosynthetic processes. They also play an important role in the binding of toxic free radicals, accelerate ammonia elimination and production of glutation in the liver. Together with the elements selenium and zinc which also provide positive liver protective functions in the described combination, they provide a new medicament especially valuable in the detoxificiation and protection against toxic challenge of the liver.

The new liver protective preparation of the invention is preferably administered orally in the form of capsules and parenterally in the form of an infusion. For oral administration, the average daily dose for adult patients can be 1.00 g L-Asparaginic acid, 0.50 g L-Cysteine, 2.00 g L-Glutaminic acid, 200.0 µg sodium selenate and 0.150 g zinc acetate.

A parenteral administration in the form of an infusion can provide an average daily dose for an adult patient of 2.00 to 6.00 g of L-Asparaginic acid, 0.50 to 2.00 g of L-Cysteine, 5.00 to 20.00 g of L-Glutaminic acid, 50.00 to 500.00 µg sodium selenate and 0.10 to 0.30 g of zinc acetate.

The treatment duration and daily dosage is, of course, dependent upon the degree of seriousness of the liver dysfunction. Patients with developed alcohol hepatitis and signs of incipient liver insufficiency are treated initially with infusion solutions and the treatment is followed over several months with capsules orally. Veterinary dosage can be determined in terms of body weight.

The average daily dose per kg of body weight is 0.015 g L-Asparaginic acid, 0.0075 g L-Cysteine, 0.03 g L-Glutaminic acid, 3.00 µg sodium selenate and 2.0 g of zinc acetate.

SPECIFIC EXAMPLES

Example 1

A capsule is formed as follows and contains:

| | |
|---|---|
| L-Asparaginic acid | 0.150 g; |
| L-Cysteine | 0.100 g; |
| L-Glutaminic acid | 0.250 g; |
| sodium selenate | 100 µg; and |
| zinc acetate | 1.050 g. |

The contents are mixed well and the mixture filled into the enterally dissolving capsules.

Example 2

The infusion solution is formed from the following composition per 1000 ml of solution

| | |
|---|---|
| L-Asparaginic acid | 4.0 g; |
| L-Cysteine | 1.0 g; |
| L-Glutaminic acid | 9.0 g; |
| sodium selenate | 200 µg; and |
| zinc acetate | 0.100 g. |

These ingredients are dissolved in a standard infusion solution, for example, a 5% dextrose solution, as a vehicle and sterilized.

Example 3

Similarly, an infusion solution is prepared from the following ingredients per 1000 ml of the resulting solution:

| | |
|---|---|
| L-Asparaginic acid | 4.00 g; |
| L-Cysteine | 2.00 g; |
| L-Glutaminic acid | 10.00 g; |
| sodium selenate | 200.00 µg; and |
| zinc acetate | 0.10 g. |

We claim:

1. A pharmaceutical composition for the treatment of a liver disorder, comprising as an effective agent against liver dysfunction, a mixture in effective amounts of the components:

(a) L-Asparaginic acid;
(b) L-Cysteine;
(c) L-Glutaminic acid;
(d) sodium selenate; and
(e) zinc acetate or zinc sulfate.

2. The pharmaceutical composition defined in claim 1 wherein said components (a) through (e) are present in the following proportions: 0.020 to 2.00 : 0.025 to 1.00 : 0.025 to 5.00 : $28 \cdot 10^{-6}$ to $500 \cdot 10^{-6}$ : 0.010 to 0.300 by weight.

3. The pharmaceutical composition defined in claim 2 in a dosage form comprising a capsule containing substantially 0.150 g L-Asparaginic acid, 0.100 g L-Cysteine, 0.250 g L-Glutaminic acid, 100 μg sodium selenate and 0.050 g zinc acetate.

4. The pharmaceutical composition defined in claim 2 in a dosage form comprising an infusion solution which contains, per 1000 ml, substantially 4.0 g L-Asparaginic acid, 1.0 g L-Cysteine, 9.0 g L-Glutaminic acid, 200 μg sodium selenate and 0.100 g zinc acetate.

5. The pharmaceutical composition defined in claim 2 in a dosage form comprising an infusion solution which contains, per 1000 ml, substantially 4.00 g L-Asparaginic acid, 2.00 g L-Cysteine, 10.00 g L-Glutaminic acid, 200 μg sodium selenate and 0.10 g zinc acetate.

6. A method of treating liver dysfunction, comprising the step of administering to an affected subject an effective amount of a pharmaceutical composition for the treatment of a liver disorder, comprising as an effective agent against liver dysfunction, a mixture in effective amounts of the components:
(a) L-Asparaginic acid;
(b) L-Cysteine;
(c) L-Glutaminic acid;
(d) sodium selenate; and
(e) zinc acetate or zinc sulfate.

7. The method defined in claim 6 wherein said component (a) through (e) are present in said composition in the following proportions: 0.020 to 2.00 : 0.025 to 1.00 : 0.025 to 5.00 : $28 \cdot 10^{-6}$ to $500 \cdot 10^{-6}$ : 0.010 to 0.300 by weight.

8. The method defined in claim 7 wherein said pharmaceutical composition is administered orally in a dosage form comprising a capsule containing substantially 0.150 g L-Asparaginic acid, 0.100 g L-Cysteine, 0.250 g L-Glutaminic acid, 100 μg sodium selenate and 0.050 g zinc acetate.

9. The method defined in claim 7 wherein said pharmaceutical composition is administered parenterally in a dosage form comprising an infusion solution which contains, per 1000 ml, substantially 4.0 g L-Asparaginic acid, 1.0 g L-Cysteine, 9.0 g L-Glutaminic acid, 200 μg sodium selenate and 0.100 g zinc acetate.

10. The method defined in claim 7 wherein said pharmaceutical composition is administered parenterally in a dosage form comprising an infusion solution which contains, per 1000 ml, substantially 4.00 g L-Asparaginic acid, 2.00 g L-Cysteine, 10.00 g L-Glutaminic acid, 200 μg sodium selenate and 0.10 g zinc acetate.

* * * * *